United States Patent [19]

Brown et al.

[11] Patent Number: 4,782,046

[45] Date of Patent: Nov. 1, 1988

[54] ULTRAPURE HYALURONIC ACID AND METHOD OF MAKING IT

[75] Inventors: Karen K. Brown, Kansas City, Mo.; Linda L. C. Ruiz, Lenexa, Kans.; Ivo Van De Rijn, Winston-Salem, N.C.

[73] Assignee: Mobay Corporation, Pittsburgh, Pa.

[21] Appl. No.: 910,246

[22] Filed: Sep. 18, 1986

Related U.S. Application Data

[60] Continuation of Ser. No. 801,973, Nov. 26, 1985, which is a division of Ser. No. 555,224, Nov. 25, 1983, abandoned.

[51] Int. Cl.$^4$ .................... C08B 37/08; A61K 31/725
[52] U.S. Cl. ...................... 514/54; 536/55.1
[58] Field of Search .......................... 514/54; 536/55.1

[56] References Cited

U.S. PATENT DOCUMENTS

| | | | |
|---|---|---|---|
| 2,599,172 | 6/1952 | Hadidian | 536/55.1 |
| 2,975,104 | 3/1961 | Warren | 195/28 |
| 3,396,081 | 8/1968 | Billek | 536/55.1 |
| 4,141,973 | 2/1979 | Balazs | 536/55.1 |
| 4,303,676 | 12/1981 | Balazs | 424/399 |
| 4,328,803 | 5/1982 | Pape | 128/276 |

FOREIGN PATENT DOCUMENTS

| | | | |
|---|---|---|---|
| 0143393 | 6/1985 | European Pat. Off. | 514/54 |
| 1617447 | 9/1970 | Fed. Rep. of Germany | 514/54 |
| 0197608 | 8/1976 | Japan | 514/54 |
| 0037001 | 3/1983 | Japan | 536/55.1 |
| 0057319 | 4/1983 | Japan | 514/54 |

OTHER PUBLICATIONS

Infection and Immunity, Feb. 1980, vol. 27, No. 2, pp. 444–448, "Growth Characteristics of Group A Streptococci in a New Chemically Defined Medium".

J. Gen. Microbiol., 1974, 85, Pt. 2, 372–5, "The Capsule of *Streptococcus equi*", (Abstract No. 121419v also enclosed).

Acta. Path. Microbiol. Scand., Sect. B, 84, 162–164, 1976, "Isolation of Hyaluronic Acid from Cultures of Streptococci in a Chemically Defined Medium", (CA 85:16770s, vol. 85, 1976 also enclosed).

Merck Index, 9th Ed., (3rd Printing), 1978, p. 537.

Arch. Ophthal—Vol. 88, (1972), pp. 544–548, David S. Swann.

*Primary Examiner*—Ronald W. Griffin
*Attorney, Agent, or Firm*—Gene Harsh; Joseph C. Gil; Lyndanne M. Whalen

[57] ABSTRACT

Hyaluronic acid having controlled molecular weight and substantially free of protein and nucleic acids can be prepared from a hyaluronidase-negative or hyaluronidase inhibited microbiological source. Product may be used as replacement fluid in mammals.

4 Claims, 4 Drawing Sheets

ULTRAPURE HYALURONIC ACID AND METHOD OF MAKING IT

This application is a continuation of application Ser. No. 801,973 filed Nov. 26, 1985 which in turn is a division of U.S. Ser. No. 555,224 filed Nov. 25, 1983, now abandoned.

RELATED APPLICATION

Patent application Ser. No. 555,310, filed Nov. 25, 1983 which is still pending, in the names of Karen K. Brown and Harold Cooper and entitled, "The Use of Ultrapure Hyaluronic Acid to Improve Animal Joint Function".

BACKGROUND OF THE INVENTION

1. Field:

This disclosure is concerned generally with the preparation, purification and use of hyaluronic acid and its salts and specifically with the preparation of hyaluronic acid from a microbiological source.

2. Prior Art:

Hyaluronic acid is a naturally occurring high molecular weight polysaccharide having an empirical formula of $(C_{14} H_{20} N Na O_{11})n$ where $n > 1000$. The general structure of hyaluronic acid is illustrated in Merck Index, Ninth Ed. (3rd printing, 1978), at page 624. It is well known that hyaluronic acid and its salts, hereafter collectively referred to as HA, can be obtained from at least three sources: human umbilical cords, rooster combs and certain bacterial cultures such as group A and C hemolytic streptococci. To the best of our knowledge, however, only umbilical cords and rooster combs are used as sources for commercially available HA. This is somewhat surprising in view of certain disadvantages associated with using those two sources (e.g. relatively low yields, contamination with chondroitin sulfate, and labor intensive processing and purification steps).

Since HA is found in aqueous and vitreous humor and the synovial fluid of mammalian joints, there has been considerable interest in obtaining purified HA for use as a fluid replacement to correct pathological conditions in the eye and in joints. The preparation of HA from rooster combs and human umbilical cords and its use in eye and joint applications is described in U.S. Pat. No. 4,141,973 to E. A. Balazs. That patent also provides a detailed review of the technical literature describing the isolation, characterization and uses of HA.

U.S. Pat. No. 4,303,676, also to E. A. Balazs, describes cosmetic formulations containing sodium hyaluronate fractions in various molecular weight ranges made from rooster combs. U.S. Pat. No. 4,328,803 to L. G. Pape discloses the use of an ultrapure hyaluronic acid salt in eye surgery. The HA product used was a sodium hyaluronate salt available under the registered trademark HYARTIL® from Pharmacia, Inc. and obtained in commercial quantities from rooster combs.

The only literature found which describes extraction of hyaluronic acid from bacteria (see Kjem and Lebech, Acta Path. Microbiol. Scand. Sect. B, 84:162-164, 1976) uses a media and process which are unacceptable for some purposes. The described media will not support growth of most Streptococci. The described process begins with heat killing the Streptococci. This extracts the organisms, releasing numerous internal contaminants which are more likely to be reactive and which are difficult to remove from the final product. Therefore, it is likely the resulting HA could not be used for injection into mammals.

Because the medical applications of HA require that the HA be injected into a mammalian body (e.g. as a fluid replacement), it is very important that the injected products be as pure as possible to avoid reactivity problems. This importance of purity is described in U.S. Pat. No. 4,141,973 which describes an ultrapure HA product prepared from rooster combs or, alternatively, from human umbilical cords. In addition to purity, it appears that control of molecular weight of an HA product is very important (e.g. the 4,141,973 patent suggests an average molecular weight of at least 750,000 and U.S. Pat. No. 4,303,676 suggests having two distinct fractions of controlled molecular weight, one low and one high). Although there is a description of a high molecular weight (1,200,000) HA preparation of very high purity (i.e. less than 0.05% protein) in a paper by Swann, Arch. Opthal. 88, pp. 544-8 (1972), we are unaware of any description of an HA product having the following advantages: (1) derivable from a microbiological source at relatively low costs, in high yields, and with low reactivity upon injection; (2) having a desirably high and closely controlled average molecular weight; and (3) being substantially free of protein and nucleic acid impurities. Quite surprisingly, we have found it is now possible to prepare such a product. Details of its preparation, characterization, and use are described below.

SUMMARY OF THE INVENTION

Our method of preparing an ultrapure HA preparation of controlled high average molecular weight comprises the steps of culturing an HA-producing, hyaluronidase-negative or hyaluronidase-inhibited organism under conditions sufficient to enhance HA content in the culture, releasing the HA from the cells, and purifying the released HA to remove substantially all protein and nucleic acids. In preferred embodiments, the HA is prepared from a group C streptococcal organism (such as *Strep. equi*), preferably cultured in a medium free of extraneous proteins, with the final product being a sterile preparation having a tightly controlled average molecular weight and containing less than about 1.25 mg/l of protein (preferably less than about 0.10 mg/ml) and less than about 45 µg/ml of nucleic acids (preferably less than about 5 µg/ml), and is used (for example) as a synovial fluid replacement in mammals.

SPECIFIC EMBODIMENTS

As shown in the examples below, the HA product of this disclosure is different from commercially available HA products in that it is made from a hyaluronidase-negative or hyaluronidase-inhibited microbiological source, has a tightly controlled average molecular weight and, very importantly, is substantially free of proteins and nucleic acids, and contains no chondroitin sulfate, all of which are considered undesirable contaminants in any product intended for replacement of an animal fluid. As used herein, the expression "substantially free of", when applied to the protein and nucleic acid content of an HA preparation, means that the protein content of the product is less than about 1.25 mg/ml (preferably less than about 0.10 mg/ml) and the nucleic acid content is less than about 45 µg/ml (preferably less than about 5 µg/ml). The expression closely controlled high molecular weight means that at least 98% of the HA is within a given high average molecular weight range (preferably from about 2.0 million (MM) to about 4.0 MM, and represented by an essentially single, substantially symetrical molecular weight distribution peak via the HPLC technique described below). Hyaluronidase-negative means that no measurable amounts of extracellular hyaluronidase (able to degrade HA to small molecules) are associated with the organism. Hyaluronidase-inhibited means that an inhibitor such as heat or enzyme inhibitors has been used so as to eliminate the breakdown of HA to smaller molecules.

In the examples below, the purity and efficacy of the HA prepared according to this disclosure was demonstrated and compared with existing commercial HA products by using the HA as a joint fluid replacement in the horse. It can be appreciated that the product can also be used in any applications in other mammals, including humans, which call for the use of a highly purified HA preparation as a fluid replacement or for other purposes such as cosmetics.

In the specific illustrative preparation steps given below, we used a known group C streptococcal HA producer (*Strep. equi*) and, by novel culturing and purification techniques, we demonstrate how it is now possible to obtain an ultrapure product of controlled molecular weight with very large yields (e.g. Avg. 31% w/w vs 0.079% w/w from rooster combs), thus providing the advantages of higher purity and better product molecular weight control with the clear advantages of economy. A sample of the *Strep. equi* strain used below has been deposited with the American Type Culture Collection, Rockville, MD 20852 as A.T.C.C. No. 39,506.

As noted above, it has long been known that HA is a major component of the capsule of Types A and C streptococci. A representation of a streptococcal organism illustrating the capsular location (hyaluronate capsule) of HA has been published by Beachey and Stollerman and is shown in *Trans. Assoc. Am. Physicians Phila.*, 85:212-221, 1972.

As has been demonstrated, the HA capsule is the outermost component making up a large portion of the total streptococcal cell. During growth of a streptococcal culture such capsule may be observed after india ink staining of the culture as a bright halo around each cell. As a result of this procedure it has been determined that maximum capsule production is obtained from several strains of streptococci grown in controlled fermentation systems by about 4 to 6 hours after the beginning of log phase growth. During late log and stationary phase the visible capsule disappears. It is known that in some strains of streptococci this disappearance of capsule is due to enzyme degradation by hyaluronidase. In long-term fermentation studies (2-5 days growth) with at least one group C streptococci (*Strep. equi*) in which pH, temperature, and glucose levels were controlled, we have determined that yields of HA can be substantially increased even though, surprisingly, the capsule is not visibly apparent in the culture. In such studies it was concluded that this strain probably lacks hyaluronidase. Thus, when extracellular hyaluronidase negative strains of streptococci are grown under controlled conditions specific for HA production, yields of an extraordinarily pure, high specific molecular weight HA have been reached and this lack of the hyaluronidase enzyme is considered an important aspect of the HA preparation.

As indicated, this invention describes the process for obtaining such high yields of extraordinary quality, high molecular weight hyaluronic acid from bacteria such as Streptococci and a method of use of such HA to replace synovial fluid from diseased joints in order to reduce lameness and swelling of such joints.

In our best examples, fermentation of a Group C streptococcus was continued at a pH between 7.0 and 7.2 for from 24 hours to 120 hours at 37° C. A special chemically defined media, described by I. van de Rijn in *Infect. and Immun.*, 27:444-448, 1980, was used for growth. This media is preferable since it contains no extraneous proteins which would have to be removed in later purification steps. Dextrose is added at 24 hour intervals to serve as a carbon source. The culture may be grown under intermittent pH control, adjusting to pH 7.6 at each addition of dextrose. Approximately 12 hours before harvest, the pH controller is shut off and the pH is allowed to drop to 6.5 to 6.8 where the culture stops growing. This allows more efficient centrifugation and somewhat better yields of hyaluronic acid.

At harvest, at least 0.01% sodium lauryl sulfate (SLS), or an equivalent anionic detergent, is added to the culture in order to release hyaluronic acid from the cells. After at least 15 mins., the SLS culture is titrated for floc formation after addition of varying amounts of a 10% solution of hexadecyltrimethylammonium bromide, or equivalent non-ionic detergent.

Generally, between 100 ml and 400 ml of this second detergent is added to 10 l of SLS culture in order to precipitate HA and SLS. After allowing at least 1 hour for maximum floc formation the precipitate is collected via centrifugation or sieve filtration. This precipitate is then solubilized in 2M $CaCl_2$ of approximately 1/10 to 1/20 the original volume. Solubilization is carried out for at least 6 hours at 4°-30° C. The resulting suspension is centrifuged or sieve filtered in order to remove the precipitate which contains cellular contaminants and both detergents. The supernate is saved and extracted with 2 volumes of a suitable alcohol (95% EtOH or 99% isopropanol preferred). A gelatinous precipitate forms which is collected after at least 1 hour via centrifugation or sieve filtration. The precipitate is solubilized overnight at 4° C-10° C. in deionized, distilled water approximately 1/10 to 1/20 the original volume. The suspension is centrifuged or sieve filtered to remove the precipitate. One percent NaCl (w/v) is added to the supernate and dissolved. Then, 2 volumes of an appropriate alcohol are added to reprecipitate the HA. Such precipitate is allowed to settle at least one hour after which it is collected via centrifugation or sieve filtration.

The solubilization of the HA in water followed by 1.0% NaCl addition and alcohol precipitation are continued in increasingly smaller volume (1/20–1/100 original volume) until the HA-water solution is clear. This usually requires at least four additional alcohol precipitation steps. An outline of the process is shown below.

OUTLINE OF PROCESS FOR EXTRACTION OF BACTERIAL HYALURONIC ACID

1. Grow Streptococcus organism
2. 1 ml/1 SLS 10%
3. 10–40 ml/1 Hexadecyltrimethylammonium bromide 10%
4. Collect ppt.
5. Solubilize in 2M $CaCl_2$
6. Collect supernate
7. 2 Vol. alcohol (ppt. HA, some nucleic acids, some protein)
8. Collect ppt.
9. Solubilize ppt. in DI-$H_2O$
10. Discard undissolved ppt.
11. Collect supernate
12. 1% NaCl
    2 Vol. alcohol
    (ppt. HA)
13. Collect ppt.
14. Solubilize in DI-$H_2O$
15. Discard ppt.
    Collect supernate
16. 1% NaCl
    2 Vol. alcohol
    (ppt. HA)
17. Collect ppt.
18. Solubilize in DI-$H_2O$
19. Discard ppt.
    Collect supernate
20. Filter - protein binding type (e.g., nitrocellulose) (remove some of the minimal protein remaining)
21. 1% NaCl
    2 Vol. alcohol
    (ppt. HA)
22. Collect ppt.
23. Solubilize 0.15M phosphate buffered saline pH 7.2
24. Adjust to 1% HA by spectrophotometric assay
25. Sterilize with 0.1% betapropiolactone 4°–10° C. 24–48 hours
26. Hydrolize betapropiolactone 37° C. 24–48 hours
27. Fill Syringes The final steps of product preparation may involve washing with 95% EtOH and 99% acetone followed by drying under vacuum. The dried HA is resuspended in 0.15M sodium phosphate buffer to a concentration of 1.0%. This may be filter sterilized through a final 0.45% nitrocellulose type filter and/or sterilized in final bulk form with 0.1% betapropiolactone. The betapropiolactone sterilization is conducted at 4° C. for 24–48 hours followed by hydrolization of the betapropiolactone at 37° C. for 24–48 hours. The final product contains 10 mg/ml HA in 0.15M sodium phosphate buffer. When these steps are followed, HA of the highest purity is obtained in high yield (>99.90% HA).

As an example of yield, an average 10 l fermenter of Strep. equi produces 5 g to 7 g dry weight of cells and 1.0 g to 2.5 g dry weight of HA. Yield is therefore between 14.3% and 50% (w/w). Yields of HA from extraction of rooster combs as in U.S. Pat. No. 4,141,973 are reportedly around 0.079%.

It should be noted that a latter-stage filtration through a suitable protein-binding filter (for example a nitrocellulose filter) is necessary in order to remove reactivity of the final product HA. Other types of filters (plain cellulose and cellulose acetate) do not adequately remove reactivity as observed in the horse joint injection test. It is thought that this step removes the minute quantity of reactive proteinaceous material remaining in the HA.

The purity of our bacterial-derived HA has been proved via a colorimetric protein assay, U.V. spectrophotometry, HPLC, and slab gel electrophoresis. Initial experiments involved quantitation of protein contamination as measured via the BIO RAD Protein Assay. This method can detect levels of protein as low as 200 ug/ml. Table I lists the results of testing aqueous 1.0% solutions of hyaluronic acid extracted from four different fermenters of Strep. equi.

TABLE I

| | BIO RAD Protein Assay Results | |
|---|---|---|
| Sample | O.D. at 595 m$\mu$ | Concentration of Protein |
| Ferm 1 | 0.00, 0.000 | <200 ug/ml |
| Ferm 2 | 0.00, 0.010 | <200 ug/ml |
| Ferm 3 | 0.00, 0.005 | <200 ug/ml |
| Ferm 4 | 0.00, 0.005 | <200 ug/ml |

According to such data, the protein content of a 1.0% bacterial-derived HA solution may be as high as 0.001%.

A second method of determining protein, peptide, and/or amino acid content is UV absorption at 280 m$\mu$. A known concentration of Bovine Serum Albumin was used as a control. Table II compares these results with UV absorption of the same solutions at 257 m$\mu$. Absorption at 257 m$\mu$ represents contamination with nucleotides or nucleic acid such as DNA and RNA. It is noted that spectrophotometric absorption at 280 m$\mu$ detects more protein contamination than the Bio RAD assay. The 1.0% solutions of bacterialderived HA contain at most 0.12% contaminants which absorb at 280 m$\mu$. Since these same solutions contain no nucleic acid contamination, the purity is in the range of at least 99.88%. In this respect it is notable that amino acid analysis of similarly extracted HA indicated the presence of <0.04% protein. This would mean that the HA purity is as high as 99.96%. This is compared with the purity of commercially available rooster comb derived HA (HYARTIL ®) available from Pharmacia or Hyalovete available from Trans Bussan) which, according to our tests, have purities in the range of 99.78% to 99.86% respectively.

TABLE II

PROTEIN AND NUCLEIC ACID CONTAMINATION OF 1.0% HYALURONIC ACID AS MEASURED BY UV SPECTROPHOTOMETRY

| | UV Absorbence | | Concentrations | |
|---|---|---|---|---|
| | | | | Nucleic |
| Sample | O.0. at 280 m$\mu$ | O.0. at 257 m$\mu$ | Protein mg/ml | Acid ug/ml |
| Ferm 1 | 0.45 | 0.00 | 0.66 | 0.0 |
| Ferm 2 | 0.83 | 0.00 | 1.22 | 0.0 |
| Ferm 3 | 0.75 | 0.00 | 1.10 | 0.0 |
| Ferm 4 | 0.47 | 0.00 | 0.69 | 0.0 |
| Miles Labs. (Rooster Comb) | 1.16 | 1.31 | 1.70 | 48.5 |

TABLE II-continued
PROTEIN AND NUCLEIC ACID CONTAMINATION OF 1.0% HYALURONIC ACID AS MEASURED BY UV SPECTROPHOTOMETRY

|  | UV Absorbence | | | Concentrations | |
|---|---|---|---|---|---|
| Sample | O.D. at 280 mµ | O.D. at 257 mµ | Protein mg/ml | Nucleic Acid ug/ml | |
| low purity Pharmacia HYARTIL ® | 0.91 | 1.63 | 1.33 | 60.3 | |
| Trans Bussan Hyalovet ™ | 1.27 | >2.0 1/30 dil. = 0.27 | 1.86 | >74<300 | |

Further studies on purity were conducted with the bacterial-derived HA. Effectiveness of two alcohol purification processes were followed spectrophotometrically at 280 mµ, 257 mµ, and 195 mµ. Absorbence at 195 mµ represents the actual absorbence of HA and is linerally related to concentration of HA. Table III shows optical density results whereas Table IV converts all readings to concentrations of protein, nucleic acid and HA. These two more recent fermenters yielded bacterial-derived HA which was 99.99% pure using either 95% E+OH for extraction or using 99% isopropyl alcohol.

TABLE III
PROOF OF PURIFICATION OF HYALURONIC ACID SOLUTIONS - UV ABSORBENCE

|  | U.V. Absorbence | | | | | |
|---|---|---|---|---|---|---|
|  | O.D. at 280 mµ | | O.D. at 257 mµ | | O.D. at 195 mµ | |
| Purification Step | ETOH | Isopropyl | ETOH | Isopropyl | ETOH | Isopropyl |
| 1st H₂O Solution | 0.480 | 0.442 | 0.456 | 0.341 | 0.740 | 0.643 |
| 2nd H₂O Solution | 0.215 | 0.288 | 0.204 | 0.230 | 1.00 | 0.898 |
| 3rd H₂O Solution | 0.215 | 0.155 | 0.191 | 0.182 | 1.76 | 1.82 |
| 4th H₂O Solution (Final 1%) | 0.078 | 0.070 | 0.140 | 0.120 | 1.90 | 1.82 |

TABLE IV
PROOF OF PURIFICATION - PROTEIN AND NUCLEIC ACID CONCENTRATIONS COMPARED WITH HYALURONIC ACID CONCENTRATION

|  | Concentration | | | | | |
|---|---|---|---|---|---|---|
|  | Protein mg/ml | | Nucleic Acid µg/ml | | Hyaluronic Acid mg/ml | |
| Purification Step | ETOH | Isopropyl | ETOH | Isopropyl | ETOH | Isopropyl |
| 1st H₂O Solution | 0.52 | 0.66 | 17.3 | 12.8 | 4.0 | 3.5 |
| 2nd H₂O Solution | 0.32 | 0.44 | 7.6 | 8.5 | 5.4 | 4.9 |
| 3rd H₂O Solution | 0.32 | 0.22 | 7.0 | 6.9 | 9.3 | 9.8 |
| 4th H₂O Solution (Final 1% HA in H₂O) | 0.08 | 0.10 | 5.0 | 4.3 | 10.2 | 9.8 |

Slab gel electrophoresis was used to further analyze the various 1.0 % hyaluronic acid preparations listed in Table II for nucleic acids. Such a technique can differentiate DNA from RNA. A 0.8% low endosmosis agarose containing 2 ug/ml ethidium bromide was used in conjunction with short wave UV light in order to visualize the nucleic acids after electrophoresis. DNA being of a much larger molecular weight remains near the origin whereas RNA migrates with the buffer front. Twenty-five ul samples were electrophoresed 18 hours at 90 volts in a Canalco Slab Gel apparatus. Results indicated no detectable nucleic acids in any of our four preparations or the HYARTIL ® product. The Hyalovet ™ product showed a significant amount of nucleic acid in the form of RNA.

Figure 1:
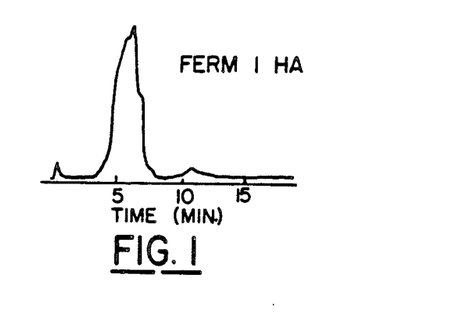
FIGS. 1-4 are graphs showing molecular weight distributions of HA made from four microbiological fermentations in accordance with the disclosures herein.
Figure 2:
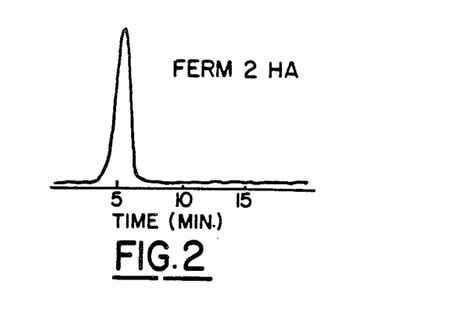
Figure 3:
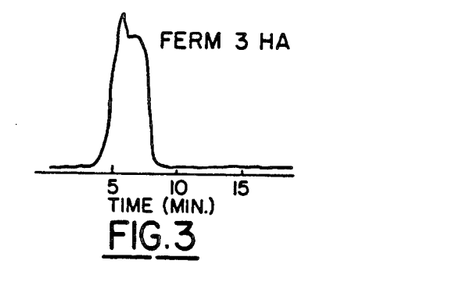
Figure 4:
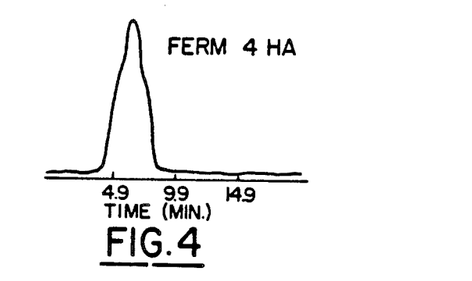
Figure 5:
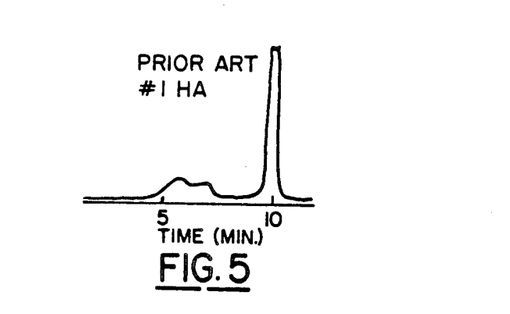
FIGS. 5-7 are graphs showing molecular weight distributions of three commercially available prior art HA preparations.
Figure 6:
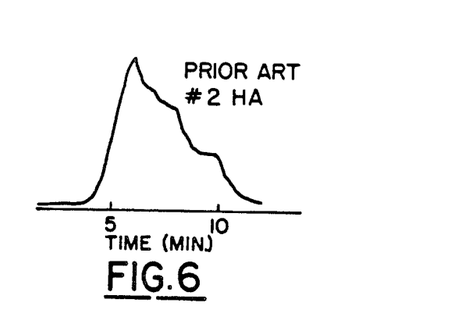
Figure 7:
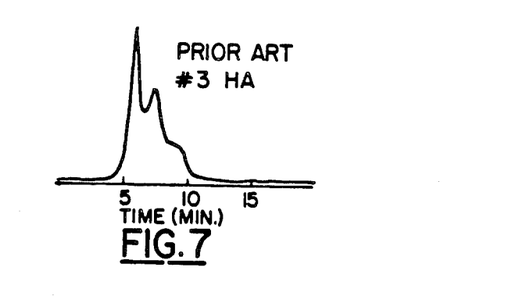

High Performance Liquid Chromatography (HPLC) was used to analyze the molecular weight of the various HA preparations. This is a newer and more accurate method than viscometry as mentioned in the U.S Pat. No. 4,141,973. To date, only one column (Waters Micro Bondagel/E-High Å) has been used for molecular weight determination. It has been impossible to run aqueous standards in the molecular weight range required along with test samples in order to determine accurate molecular weights. However, we have determined relative molecular weights based upon retention times on the column. Theoretically, with this procedure, the earlier the time of peak detection the higher the molecular weight. The column has a retention time of 10 min. with minimum and maximum molecular weight capabilities between 15,000 and 7,000,000. FIGS. 1-4 show the HPLC tracings for our first four fermenter preparations. Miles Hyaluron, Pharmacia HYARTIL ®, and Trans Bussan Hyalovet are shown in FIGS. 5-7. The retention times of the peaks and shoulders have been determined and relative molecular weights have been calculated based on a linear relationship between molecular weight (15,000 to 7,000,000) and retention time (0-10 minutes). Such relative molecular weights are listed in Table V. As can be seen in FIGS. 1-4, the HPLC separated HA of this disclosure results in an essentially single, substantially symmetrical high molecular weight (avg. higher than about 2 MM) distribution peak. In FIGS. 1-4 at least about 98% of the HA content is within the single peaks shown. Such close control of high molecular weight distribution is not shown in existing commercial products as illustrated in FIGS. 5-7. FIG. 5 (Prior Art #1) illustrates the HPLC tracing for the Miles Hyaluron HA product. FIG. 6 (Prior Art #2) represents the Hyalovet product and FIG. 7 (Prior Art #3) represents the HYARTIL ® product. It is thought that this close control of final molecular weight range may be due to the simplicity of the extraction procedure requiring minimal shear-producing steps as well as to the lack of hyaluronidase which could degrade high molecular weight HA.

TABLE V
Relative Molecular Weights of Hyaluronic Acid Moieties in Various Preparations

|  | Relative Molecular Weights in Millions | |
|---|---|---|
| Sample | Range | Average |
| Fermenter 1 | 2.2-3.9 | 2.8 |
| Fermenter 2 | 2.5-4.0 | 3.8 |
| Fermenter 3 | 1.7-2.8 | 2.4 |
| Fermenter 4 | 1.1-3.9 | 2.6 |
| Hyaluron | 0.015-3.0 | 0.015 |
| HYALOVET | <0.010-3.7 | .015, 1.8, 3.7 |
| HYARTIL ® | <0.010-3.8 | 1.9 |

As noted above the relative molecular weight range of HA moieties found in bacterial-derived HA is narrow with the majority (98%) measuring between about 1,100,000 or 2,200,000 and 4,000,000. Via the same method, Hyalovet contains three distinct molecular weight moieties of 2,700,000; 1,700,000 and 300,000. Finally, the HYARTIL ® product contained an array of HA molecular weights from <10,000 to 3,700,000. As shown, the HYARTIL ® product contains the widest variation of molecular weight sizes.

From the various analytical tests described herein, it has been determined that HA extracted from bacteria via a simple method is purer than three commercial products made from either rooster combs or umbilical cords. The latter are produced via a complex process which is inefficient yielding only 0.079% HA. This is compared with HA extracted from streptococci which can reach yields as high as 50% w/w.

Joint Fluid Replacement

Hyaluronic acid prepared from bacteria as described herein has been tested for reactivity in tibiotarsal and radialcarpal joints of horses. The following clinical index test was devised in order to measure reactivity of HA preparations post intra-articular injection of horses. The test protocol is as follows:

1. Assess normal movement of joint to be injected. Assign lameness indices from 0 to 5 according to the following definitions.

Lameness Index

0 = No lameness
1 = Slight lameness—moderate
2 = Noticeable lameness—moderate
3 = Obvious lameness
4 = Severe lameness—reluctant to move or bear weight
5 = Cannot bear weight. If down, animal is unable to rise.

2. Sedate horse (e.g. with Rompun ® sedative).
3. Shave hair around the joint area to be injected.
4. Determine Swelling Observation Index according to the following definitions.

Swelling Observation Index

0 = No swelling
1 = Nothing obvious—palpable fluid
2 = Slightly noticeable—palpable fluid
3 = Noticeable swelling of entire joint
4 = Severe swelling at injection site
5 = Severe swelling involving more than the joint alone.

5. With cloth tape measure, measure joint circumference immediately anterior to the anterior aspect of the third metatarsal (tibiotarsal joint) or immediately distal to the protuberance of the accessory carpal bone that is around the radial carpal bone (carpal joint).

The exact circumference of the joint (in millimeters) before and after injection is recorded. A difference between the circumference each day post injection and the original circumference is calculated. If the difference is greater than 1.0 cm, the exact measurement is added to the other two index values in order to determine the clinical index.

6. Remove joint fluid (1.0–2.0 cc) prior to injection with a 3.0 cc syringe with a 20–22 ga. X 1" needle.
7. Inject joint with 2.0 cc of a 1% preparation of hyaluronic acid being evaluated for reactivity. For this injection, use a 3.0 cc syringe with the same needle (exchanging syringes only) as used to remove joint fluid. This is done so as to reduce trauma to the joint as much as possible.
8. Apply digital pressure to the injection site for 1 to 3 minutes after injection. This is done to prevent backflow of the very viscous HA.
9. Observations and measurements are made for four consecutive days post injection, then on day 7.
10 The Clinical Index (CCI) is calculator as follows:

Total Lameness Index (TLI) = Sum of Daily Lameness Indices

Total Swelling Index (TSI) = Sum of Daily Swelling Observations + Sum of Joint Circumference Measurements Greater Than 1.0 cm.

CI = TLI + TSI

11. Interpretation

Joint injection alone causes trauma with development of some swelling and lameness. This was proven by evaluating numerous joints injected with phosphate buffered saline (PBS) and some joints in which only fluid was removed. CIs were calculated on these traumatized joints. They varied from 0 to 18.7 among 56 joints. However, the average CIs in the three separate studies of traumatized joints showing these wide individual variations were 0.7, 5.3, and 3.4. It is thus suggested that an average CI value of 6.0 or less in at least 10 joints could be expected from injection trauma. On this basis, we have assigned a 10 - joint average CI value of 6.0 or less as acceptable in the horse joint reactivity test for evaluation of HA preparations. Any product showing a 10 - joint average of CI of >6.0 is unacceptable. Using these criteria, several HA preparations were tested. Results are shown in Table VI.

TABLE VI

Evaluation of Hyaluronic Acid Preparations by the Horse Joint Reactivity Test

| Preparation | No. of Joints | Average CI | Acceptability of Preparation |
|---|---|---|---|
| Microbiological Source HA Filtered through Nitrocellulose | 14 | 4.6 | Acceptable |
|  | 13 | 5.5 | Acceptable |
| Microbiological Source HA Nonfiltered | 11 | 16.4 | Unacceptable |
|  | 6 | 17.4 | Unacceptable |
| Prior Art #1 Purified and Filtered | 10 | 6.2 | Unacceptable |

The microbiological source HA listed in Table V was that obtained from fermenters 1–4 as described previously. It is noteworthy that this material is acceptable for joint injection after nitrocellulose filtration but not prior to such filtration. On the other hand, Prior Art #1 (see FIG. 5) is on the borderline of being unacceptable even after nitrocellulose filtration. Evidently, the reactive proteinaceous load in the Prior Art #1 preparation is too great to be removed via the protein binding filtration step.

The same Clinical Index can be used to evaluate efficacy of treatment of diseased joints with HA. In this test system clinical symptoms are induced in joints with intraarticular injection of complete or incomplete Freund's adjuvant. This adjuvant produces first an acute and then a chronic pathology of the joint characterized by extreme lameness and swelling which does not appear to reverse itself within two months.

Some such efficacy studies have been conducted on the bacterial-derived HA Experiments.

Figure 8:
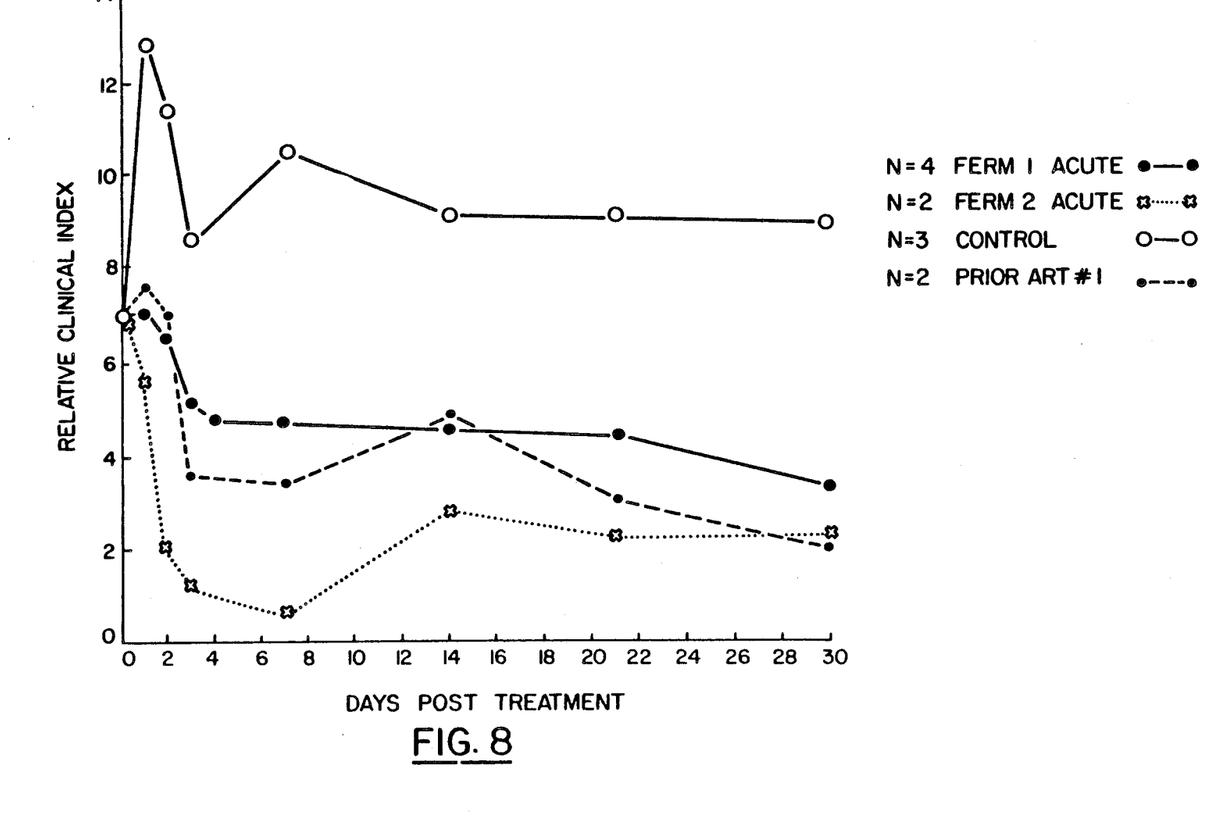
FIGS. 8-9 are graphs comparing the efficacies as a joint fluid replacement of the HA products of this disclosure with controls and/or, a commercially available product.
Figure 9:
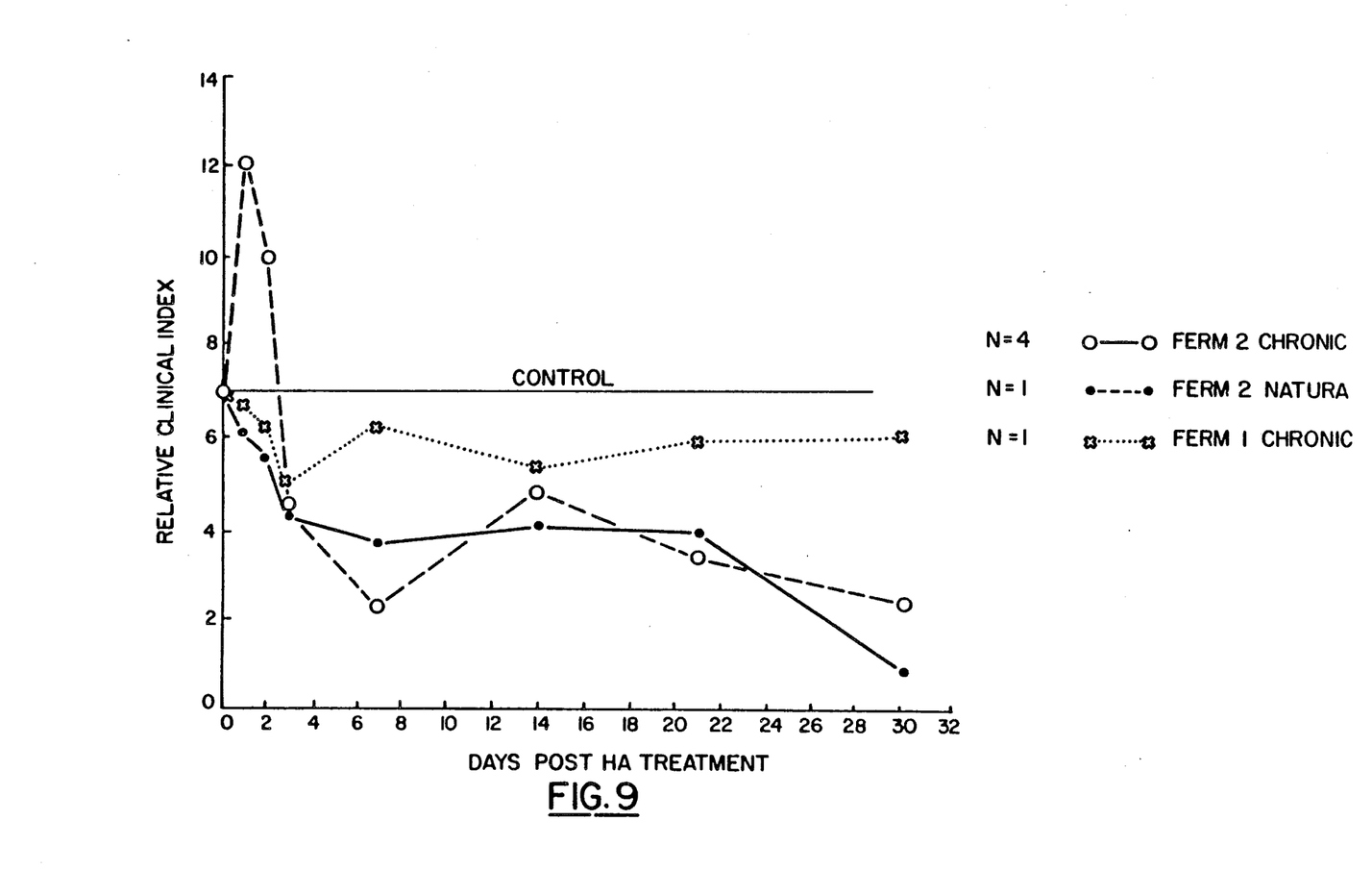

Experiments were designed to evaluate the effect of removing some of the joint fluid from adjuvant induced pathological joints and replacing it with bacterial-derived HA. This was done with both acute joints (HA injection within three days of Freund's injection and with chronic joints (HA injected within 12 to 34 days of Freund's injection). Clinical Index evaluation was begun the day of adjuvant injection and continued for four days following the HA injection after which weekly observations were made for three weeks. FIGS. 8 and 9 display the results over 30 day periods.

FIG. 8 represents the acute situation. The zero day readings were all adjusted to seven on the relative index scale so that comparisons could be better visualized. Zero day represents three days post Freund's injection in the acute joints. FIG. 8 then portrays the change in Clinical Index for the first 30 days post injection with HA from fermenters 1 and 2 and Prior Art #1 after further purification. These results are compared with similar adjuvant injected joints left untreated (control). It is notable that the control horses continually worsen through day 4 post Freund's injection before showing some improvement on their own. However, this improvement does not reach the starting level by day three and by day four appears to be plateauing. This is the typical picture for induction of chronic pathology. A significant improvement in acute symptoms is observed after injection of HA.

The chronic situation is represented by FIG. 9. Horses which had been injected with Freund's complete or incomplete adjuvant 12-34 days prior to HA treatment can serve as their own controls since these horses had been stable for at least seven days prior to day zero. The control line represents these control index levels. Again, immediate clinical improvement is noted after treatment with HA. Longer term observation of these horses has indicated that the improvement tends to plateau. Therefore, it is expected that more than one treatment may be necessary.

Figure 10:
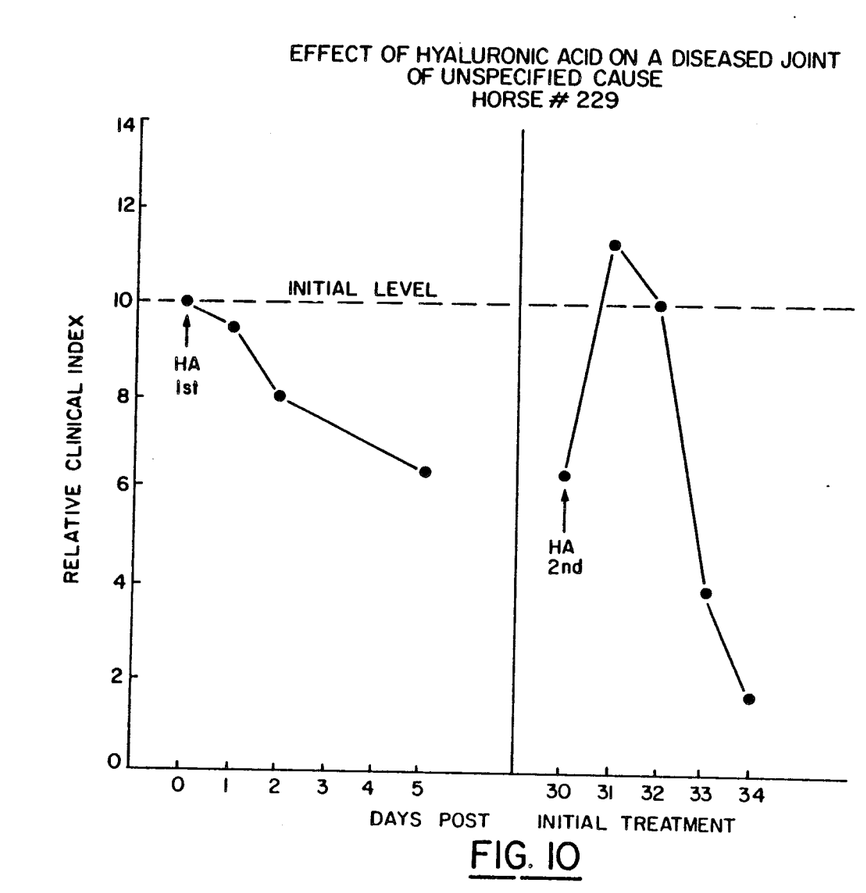
FIG. 10 is a graph showing the use of the product of this disclosure as a fluid replacement in an equine joint diseased by unspecified cause.

One horse, entered our study with a diseased joint of unspecified cause. As indicated in FIG. 10, two injections of bacterial-derived HA were administered to this joint 30 days apart. In this case, the zero day readings were adjusted to 10 in order to display the complete treatment response. Immediate improvement was noted after both the first and second, injections of HA. The improvement after the first injection was followed by some return of pathology as indicated by swelling only. After the second HA injection joint swelling was eliminated and has not returned within three months post treatment.

From the data presented herein it is obvious that ultra pure bacterial-derived HA is nonreactive in horse joints and displays efficacy for reversing lameness and/or swelling in diseased joints. Since bacterial-derived HA as described herein is purer than any commercially available product, including those used in opthalmalogical treatments, it is highly probably that these HA preparations could also be used to replace vitreous humor of the eye during surgery. They should be able to substitute for any other use applied to the rooster comb or umbilical cord HA.

Given the above disclosures, it is thought that numerous variations in our HA production methods and uses will occur to those skilled in the art. Thus, it is intended that the above-described examples should be construed as illustrative only and that the scope of the invention disclosed herein should be limited only by the following claims.

We claim:

1. A sterile preparation comprising hyaluronic acid or a salt thereof, the preparation having a protein content of less than about 1.25 mg/ml and a nucleic acid content of less than about 45 µg/ml and having a molecular weight range such that at least 98% of the preparation is within a molecular weight range of from about 2.0 million to about 4.0 million as determined by High Performance Liquid Chromatography.

2. The preparation of claim 1 wherein the preparation, when subject to High Performance Liquid Chromatography, produces an essentially single, substantially symmetrical distribution peak.

3. The preparation of claim 2 wherein the protein content is less than about 0.10 mg/ml and the nucleic acid content is less than about 5 µg/ml.

4. The preparation of claim 3 wherein the preparation has a Clinical Index of less than 6.0 as determined by the Horse Joint Reactivity Test.

* * * * *